(12) United States Patent
Paitich

(10) Patent No.: US 7,111,492 B2
(45) Date of Patent: Sep. 26, 2006

(54) DEVICE FOR TESTING BALLS

(76) Inventor: Ronald M. Paitich, 5841 Bell Rd., Auburn, CA (US) 95602

(*) Notice: Subject to any disclaimer, the term of this patent is extended or adjusted under 35 U.S.C. 154(b) by 0 days.

(21) Appl. No.: 10/890,897

(22) Filed: Jul. 13, 2004

(65) Prior Publication Data

US 2005/0044927 A1 Mar. 3, 2005

Related U.S. Application Data

(60) Provisional application No. 60/488,500, filed on Jul. 18, 2003.

(51) Int. Cl.
*G01N 3/30* (2006.01)
(52) U.S. Cl. .................... 73/12.02; 73/65.02
(58) Field of Classification Search ........... 73/12.01, 73/12.02, 79, 65.02
See application file for complete search history.

(56) References Cited

U.S. PATENT DOCUMENTS 4,509,362 A 4/1985 Lyons
5,245,862 A 9/1993 Zeiss
6,755,085 B1 6/2004 Kazanjian et al.

OTHER PUBLICATIONS

Plummer, Ian, Ph.d., "Ball Bounce Testing", *Oxford Croquet*, www.oxfordcroquet, com/tech/bounce/index.asp, 5 pgs.

*Primary Examiner*—Max Noori
(74) *Attorney, Agent, or Firm*—Dorsey & Whitney LLP

(57) ABSTRACT

A ball testing device having a compact housing with a microphone for receiving the sound generated when a ball strikes a surface and generating output signals. An electrical circuit in said housing is configured to receive the output signals and process the signals to determine the time lapse between the first and second and the second and third successive bounces of the ball and provide the ratio of time lapse between the second and third bounces to that of the time lapse between the first and the second bounce to provide the coefficient of restitution of the ball. Said housing including a display for displaying the coefficient of restitution.

8 Claims, 3 Drawing Sheets

DEVICE FOR TESTING BALLS

RELATED APPLICATIONS

This application claims priority to Provisional Patent Application Ser. No. 60/488,500, filed on Jul. 18, 2003, the disclosure of which is hereby incorporated by reference in its entirety.

BRIEF DESCRIPTION OF THE INVENTION

The invention relates to a compact, economical, portable, simple and accurate device for measuring the Coefficient of Restitution (COR) of balls such as golf balls, tennis balls, baseballs and the like.

BACKGROUND OF THE INVENTION

In the sport of golf, one element of the game is to hit the ball as far as possible and as accurately as possible. Golf balls produced by different manufacturers or with varying history will respond in varying ways to being struck by the golf club; some will travel farther than others. A significant factor in determining how far a ball will travel after being struck is the COR of the golf ball. By selecting golf balls that have a higher COR, a golfer may have his ball travel farther, resulting in an advantage over his opponents. Alternatively, a golfer may select balls that have closely matched Coefficients of Restitution, such that his golf balls will travel in a more predictable trajectory.

The United States Golf Association (USGA) performs tests of Coefficient of Restitution on golf balls. The equipment consists of an impact device driven to a known velocity, which then strikes the golf ball. Velocity of the golf ball is measured and is interpreted for the Coefficient of Restitution of the golf ball.

The American Society for Testing and Materials (ASTM) has a method defined in its standard F1887, Standard Test Method for Measuring the Coefficient of Restitution (COR) of Baseballs and Softballs. In the ASTM method, baseballs or softballs are propelled at a known velocity in a manner to strike a rigid plate. The rebound velocity is measured and is interpreted for COR of the baseball or softball. In the ASTM method, the apparatus propelling the baseball or softball requires the ball be launched with a speed accuracy of approximately 1%. Both the ASTM method and the USGA method require skilled operators and are impractical, cumbersome and excessively costly to be employed by the average sportsman or golfer.

Dr. Ian Plummer of the Oxford University croquet club has described a method used to measure the COR of croquet balls. The rebound height of the ball is measured and is interpereted for COR.

An Australian team of Richard Bowman, Peter Westgate and Elizabeth Maliwat, CSIRO Division of Building, Construction and Engineering, Highett, Victoria 3190, Australia describe a proposed procedure to test COR of ceramic tiles. The COR test apparatus consists of a ball-release apparatus, where an electromagnet releases a 19 mm diameter chrome steel ball that falls 1 meter onto the center of a horizontal test specimen that is clamped to a horizontal support base. A microphone and electronic timer computes the time interval between the first and second impacts of the dropped ball, to the nearest 0.001 second. According to their paper, the COR can be calculated from the relationship:

$$COR = (1.226 T^2)^{0.5}$$

U.S. Pat. No. 4,509,362 discloses a device in which COR is determined as a function of the height from which the ball is dropped to the rebound height. This method is not complex, but requires careful measurement by the observer, and is not easily and routinely done. In addition, it is prone to human error in observation of the rebound height.

U.S. Pat. No. 5,245,862 teaches a testing device in which the COR is determined by comparison of the bounce period of successive bounces of the ball.

These and other devices which have been proposed to test golf balls and the like are cumbersome and not suitable as compact, portable testing devices which can be easily carried and stored with other golf equipment and which can be used before and during play.

OBJECTS AND SUMMARY OF THE INVENTION

It is general object of the present invention is to provide a testing device which is inexpensive, compact, portable and simple to operate.

It is another object of the present invention to provide a device for testing the COR of a ball which will enable players to test the condition of their golf balls before and during a game.

It is a further object of the present invention to provide a device for measuring the COR of a golf ball which is entirely housed in a compact housing with a display for displaying the measured COR.

It is a further object of the present invention to provide a simple to operate, lightweight, pocket size golf gall testing device.

The foregoing and other objects of the invention are achieved by a ball testing device having a compact housing with a microphone for receiving the sound generated when a ball bounces from a surface and providing output signals. An electrical circuit in said housing receives the output signals from the microphone and is configured to process said signals to determine the time elapsed between the first and second bounces and time elapsed between the second and third bounce and provide an output signal representing the ratio of the time between the second and third bounce to the time between the first and second bounce to provide the Coefficient of Restitution. Said housing includes a display responsive to the output signal to display the Coefficient of Restitution.

BRIEF DESCRIPTION OF THE DRAWINGS

The foregoing and other objects of the invention will be more clearly understood from the following description when read in connection with the accompanying drawings of which.

DETAILED DESCRIPTION OF THE INVENTION

Figure 1:
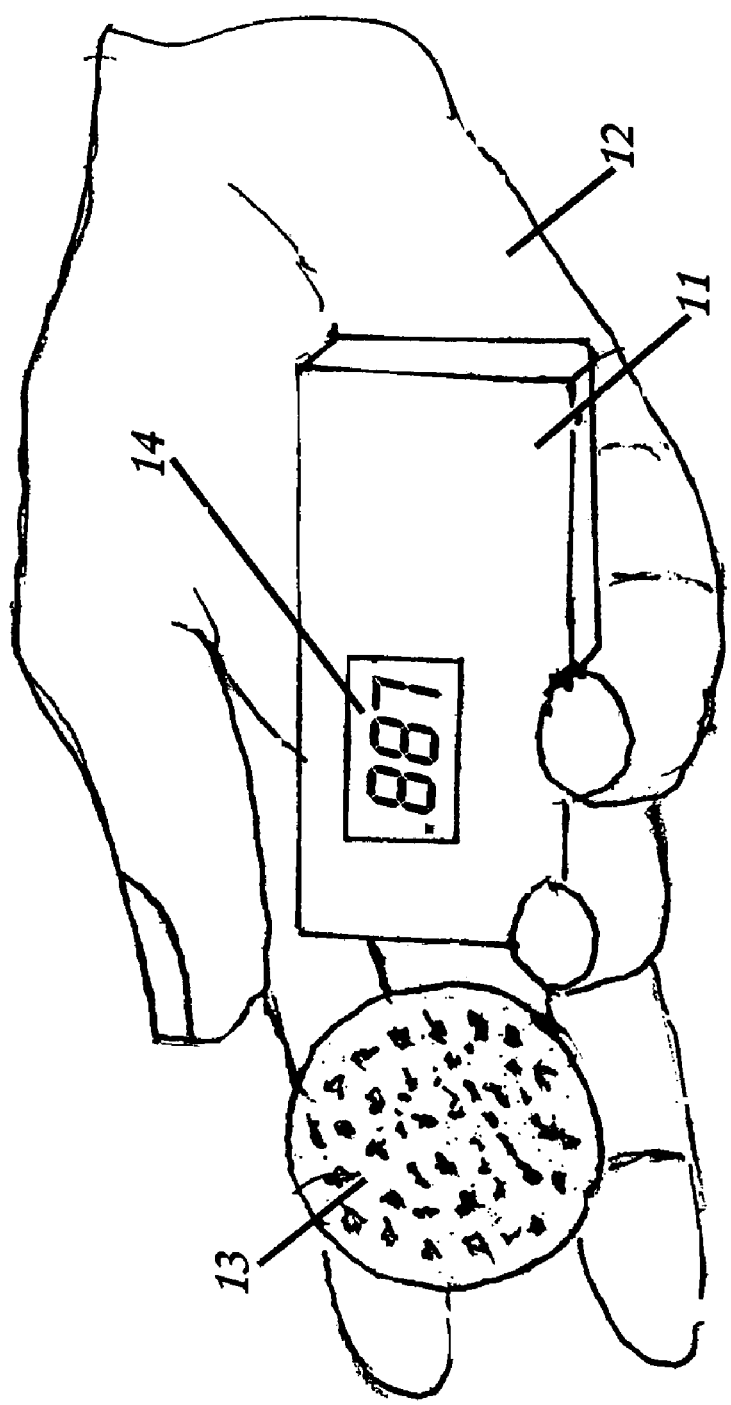
FIG. 1 shows a ball testing device in accordance with the invention held in the palm of the hand next to a golf ball.

Referring now to FIG. 1, the ball testing device 11 is shown held in the palm of a golfer's hand 12 alongside a golf ball 13. This illustrates the portability and compactness of the device. The device includes a display 14 which displays the Coefficient of Restitution.

Figure 2:
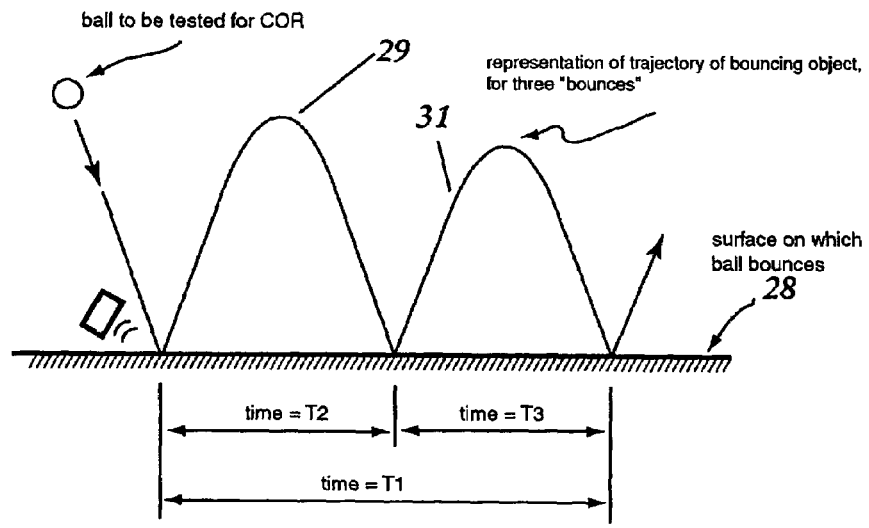
FIG. 2 is a schematic diagram showing the ball testing device oriented to receive the sound emitted by a ball as it bounces upon a surface.
Figure 3:
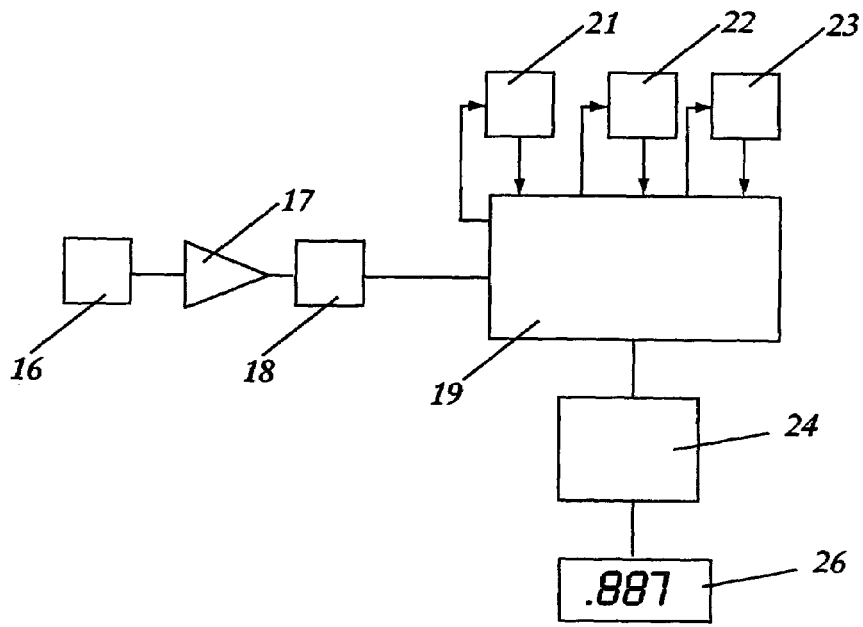
FIG. 3 is a block diagram of the electronic circuit for determining and displaying the Coefficient of Restitution.
Figure 4:
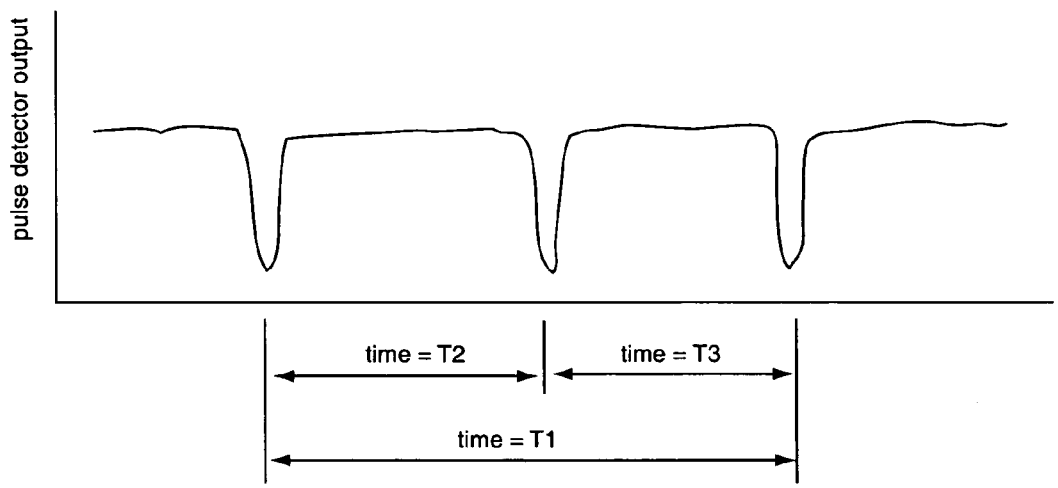
FIG. 4 represents the output of the pulse detector shown in FIG. 3.

Referring particularly to FIG. 3, the device includes a microphone 16 which provides an output signal responsive to sound emitted as the ball strikes the surface. The output of the microphone is amplified by an amplifier 17 and the output of the amplifier 17 is applied to a pulse detector 18 which detects the occurrence of each bounce and provides output pulses such as shown in FIG. 4 each time the ball bounces. The amplifier response is shaped to create a bandwidth filter optimized to the characteristic frequency of the sound of the ball striking the surface. This is to reduce background noise, thereby minimizing detection of sounds that would be erroneously detected as a bounce, but which are not associated with the test. The output pulses are applied to a timer control and computing or processing circuit 19. The circuit 19 controls the timers 21, 22 and 23. The timer control starts the timers 21 and 22 upon the occurrence of the first pulse. Upon occurrence of the second pulse, the timer stops the timer 22 and starts the timer 23. Upon the occurrence of the third pulse, timers 21 and 23 are stopped. Thus the output of the timer 21 will be time T1 between the first and third pulse, while the output of the timer 22 will be the time T2 between the first and second pulse and the output of the timer 23 will be the time T3 which is the time between the second and third pulses, see illustration FIGS. 2 and 4. The circuit processes the timer outputs to obtain the Coefficient of Restitution by calculating one of the following ratios:

$$COR=(T1-T2)/T2$$

$$COR=T3/T2$$

or $$COR=T3/(T1-T3)$$

The ratio relationship can easily be deducted from elementary physics. It is seen that only two timers are required in each instance to obtain the ratio and determine the Coefficient of Restitution.

Figure 5:
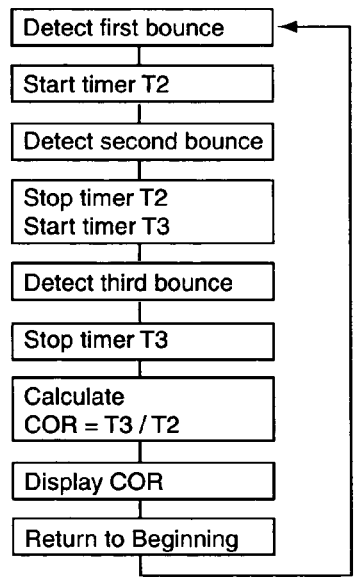
FIG. 5 is a flow diagram illustrating the signal processing to provide the Coefficient of Restitution.

This ratio is then applied to a liquid crystal display driver 24 which drives a liquid crystal display 26 to display the COR. Referring particularly to FIG. 2, as illustrated, a ball to be detected bounces on the surface 28 as illustrated by the curves 29 and 31. The testing device 111 is arranged to receive sound at each of the bounces and the times between bounces is illustrated by the T2 and T3. A summary of the operation is provided in FIG. 5 for use with timers for T2 and T3.

When using the device 11 it is important that the ball be dropped from a height which will result in at least three bounces. As a practical matter, the measurement of the Coefficient of Restitution will be less affected by air viscosity if the ball is dropped from modest heights, e.g. 0.2 meters to 0.5 meters, rather than from much greater heights, e.g. 2 meters. This effect was observed experimentally for golf balls dropped from heights of 1.5 meters to 2.5 meters. The COR was fractionally (a few percent) less than the COR for the same ball dropped from heights of 0.2 meters to 0.5 meters. We also observed that lower COR baseballs required that they be dropped from greater heights in order that the three bounces may be resolved. Otherwise the second and third bounces resulted in too short an interval for reliable measurements.

In one example, a ball testing device in accordance with the invention was constructed and housed in a housing having a size of 3.1×1.5×0.7 inches. However, this was a preproduction unit and with modem electronics and integrated circuits the size can be further reduced, thereby providing a ball testing device which can be easily held in the palm of a hand, can be carried in the pocket or in a person's golf bag along with other equipment, and which has a minimum weight.

To use the tester it is only necessary to bounce the ball on a hard surface close to the testing device. The internal microprocessor processes the received signals and then displays the COR. This is in contrast to previous methods which required elaborate, cumbersome and expensive equipment. The pocket size ball testing devices gives laboratory quality results that until now were beyond the means of the average golfer.

What is claimed is:

1. A ball testing device for use with a ball and a surface distinct from the device comprising:
   a housing adapted for use when the ball is bouncing on the surface,
   a microphone in said housing for receiving the sound generated from the ball bouncing on the surface and providing an output signal,
   an electrical circuit in said housing for receiving the output signal from the microphone for three successive bounces and providing three bounce signals, said circuit
   a) configured to process the bounce signals and determine a first time lapse between the first and second bounce and a second time lapse between the second and third bounce and
   b) further configured to obtain the ratio of the second time lapse to the first time lapse and provide a ratio signal representing the coefficient of restitution of the ball, and
   a display in said housing for providing a display of the coefficient of restitution in response to said ratio signal.

2. A ball testing device as in claim 1 in which the electrical circuit includes an amplifier with a bandwidth filter shaped to the characteristic frequency of the sound of the ball striking the surface to minimize generating signals that are not associated with bounce sounds.

3. A ball testing device as in claim 1 or 2 in which the housing is compact whereby it can easily be carried in the pocket of a user.

4. A ball testing device as in claim 3 in which the housing is 3.1×1.5×0.7 inches or less.

5. A hand-held ball testing device comprising a housing adapted to be held by a human hand and having a size for permitting the housing to be cupped in the palm of the hand, a microphone in the housing for receiving the sound generated when a ball bounces on a surface spaced from the housing and for providing an output signal, an electrical circuit in the housing and electrically coupled to the microphone for receiving the output signal for three successive bounces and for providing three respective bounce signals, the circuit being configured to process the bounce signals and determine a first time lapse between the first and second bounce and a second time lapse between the second and third bounce and to obtain the ratio of the second time lapse to the first time lapse and to provide a ratio signal representing the coefficient of restitution of the ball, and a display in the housing and electrically coupled to the circuit for receiving the ratio signal so as to display the coefficient of restitution.

6. A ball testing device as in claim 5 wherein the electrical circuit includes an amplifier with a bandwidth filter shaped to the characteristic frequency of the sound of the ball bouncing on the surface to minimize generating signals that are not associated with bounce sounds.

7. A ball testing device as in claim 5 or 6 wherein the housing has a size for permitting placement of the housing in a pocket of a user.

8. A ball testing device as in claim 7 wherein the housing is 3.1×1.5×0.7 inches or less.

* * * * *